United States Patent

Chen

[11] Patent Number: 5,868,315
[45] Date of Patent: Feb. 9, 1999

[54] AIR FRESHENER

[76] Inventor: Wen-Jye Chen, 7F-2, 293-3, Fu-Hsing S. Rd., Sec.2, Taipei, Taiwan

[21] Appl. No.: 78,310

[22] Filed: May 13, 1998

[51] Int. Cl.$^6$ ................................................. A24F 25/00
[52] U.S. Cl. .............................. 239/34; 239/57; D23/367
[58] Field of Search .................. 239/34, 57, 60; D23/366, 367

[56] References Cited

U.S. PATENT DOCUMENTS

| | | | |
|---|---|---|---|
| D. 393,901 | 4/1998 | Kuhn | D23/368 |
| 4,372,490 | 2/1983 | LeCaire, Jr. et al. | 239/59 |
| 4,890,791 | 1/1990 | Hoffman | 239/44 |
| 5,014,913 | 5/1991 | Hoyt et al. | 239/45 |
| 5,527,493 | 6/1996 | McElfresh et al. | 261/130 |

*Primary Examiner*—Kenneth Bomberg
*Assistant Examiner*—Lisa Ann Douglas
*Attorney, Agent, or Firm*—Pro-Techtor International Services

[57] ABSTRACT

An air freshener includes a top cover shell and a bottom cover shell respectively shaped like a slice of bread and pivoted together, a spring plate retained between the top cover shell and the bottom cover shell, two clamping plates shaped like a slice of vegetable leaf and a slide of cheese and respectively fastened to the top cover shell and the bottom cover shell on the inside and forced by the spring force of the spring plate to hold a cake of solid perfume in therebetween, the bottom cover shell having a tongue with a hanging hole for hanging, and a retaining hole for fastening a clip.

3 Claims, 8 Drawing Sheets

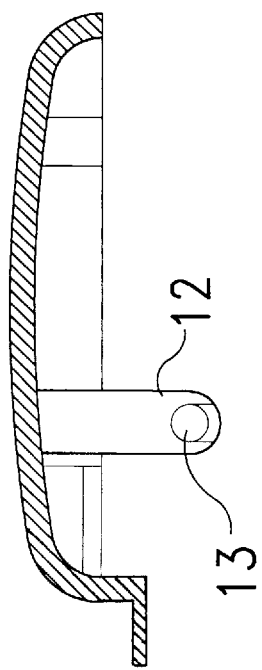

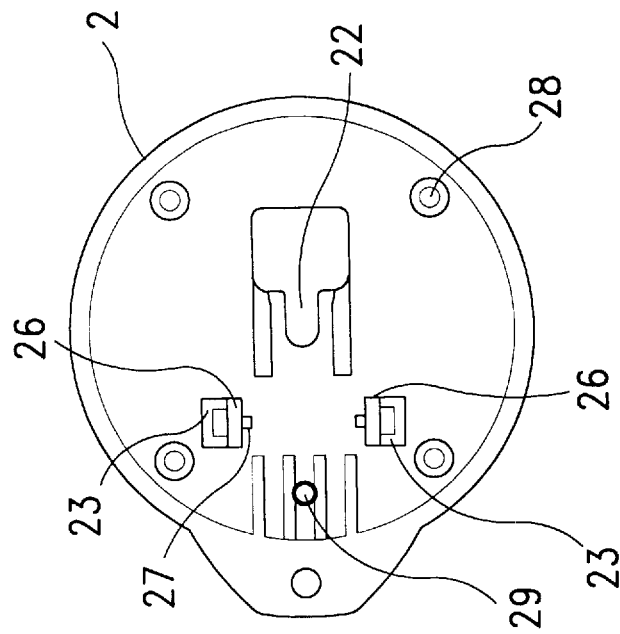
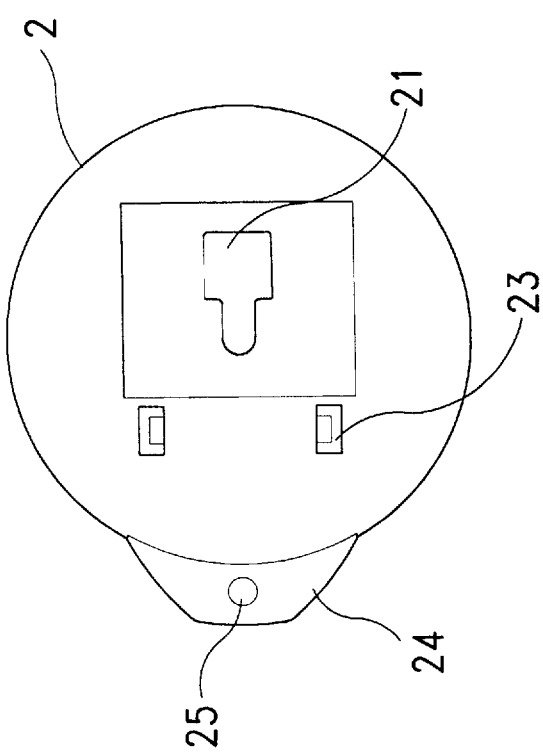

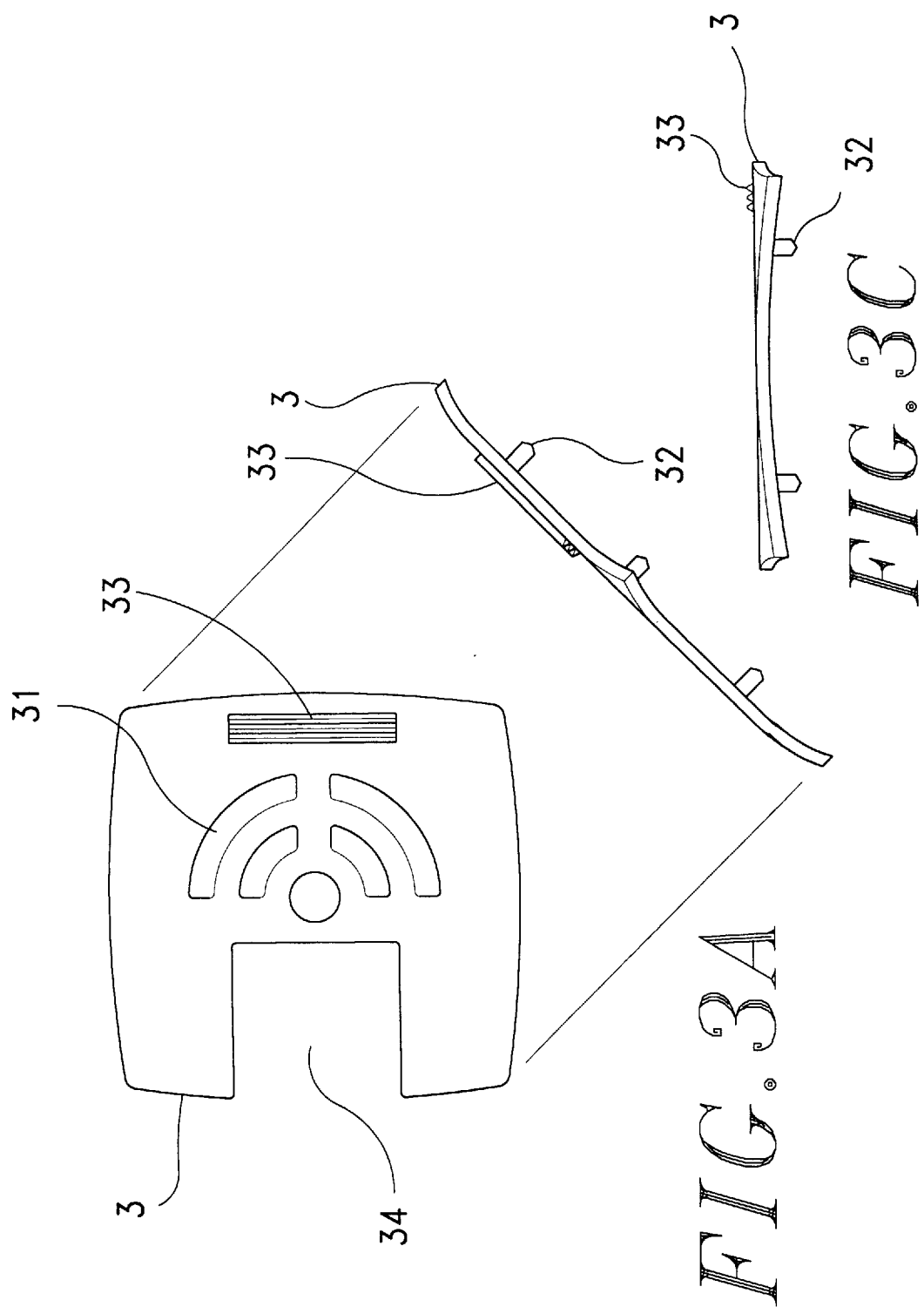

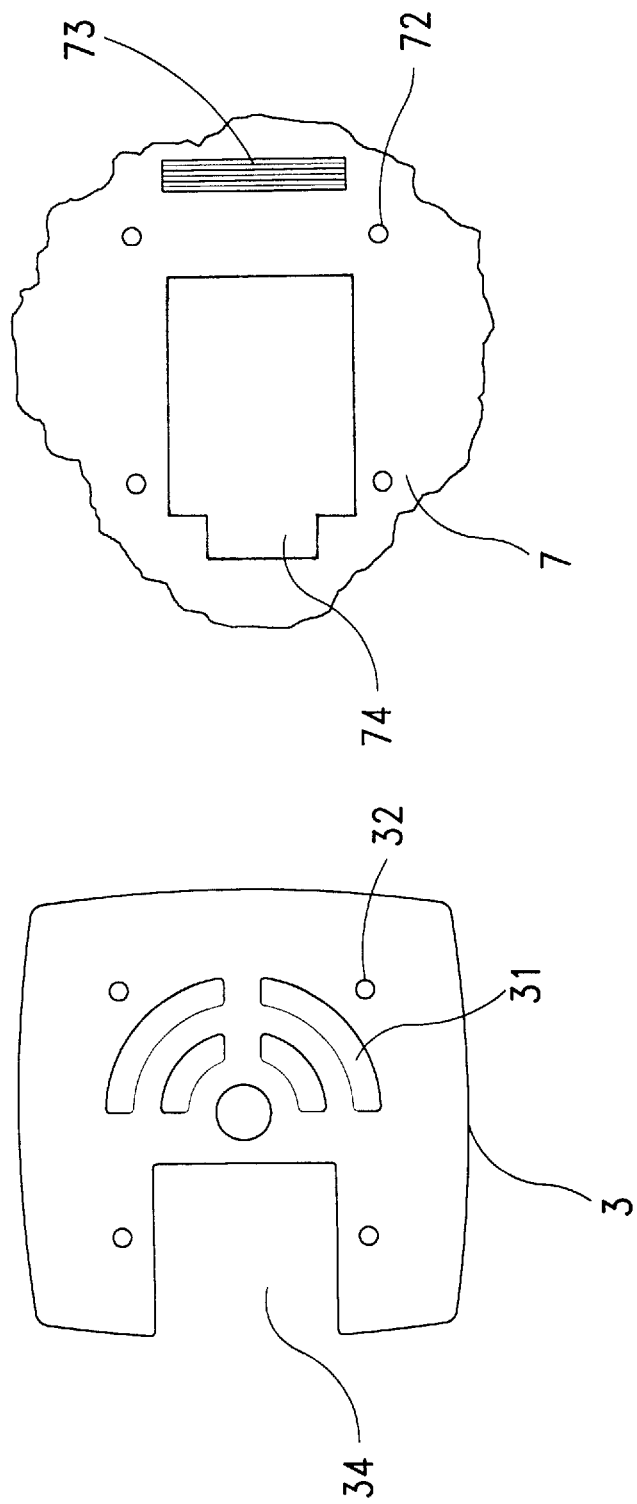

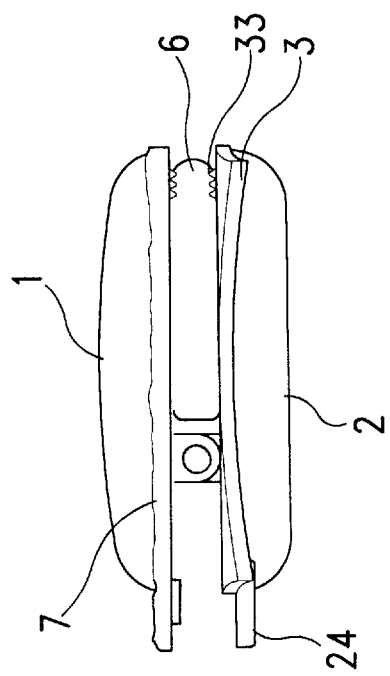
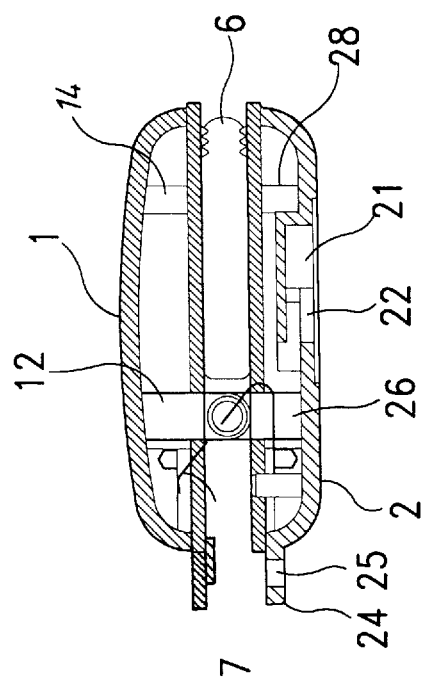

AIR FRESHENER

BACKGROUND OF THE INVENTION

The present invention relates to an air freshener, and more particularly to such an air freshener which is shaped like a sandwich that holds a cake of solid perfume between two cover shells.

Conventional air fresheners are commonly comprised of a container formed of a top cover shell and a bottom cover shell, and a perfume retained in the container. The container has air vents for ventilation. Through the air vents, good smell of the contained perfume is carried out of the container by currents of air. Conventional air fresheners are simply designed to hold a perfume, they cannot be used for any other purposes. Furthermore, when the contained perfume is used up, the container becomes useless.

SUMMARY OF THE INVENTION

It is one object of the present invention to provide an air freshener which enables the user to replace the perfume conveniently. It is another object of the present invention to provide an air freshener which can be used as a decorative item as well as a paper clip. To achieve these and other objects of the present invention there is provided an air fresheners which is comprised of a top cover shell and a bottom cover shell respectively shaped like a slice of bread and pivoted together. a spring plate retained between the top cover shell and the bottom cover shell, two clamping plates shaped like a slice of vegetable leaf and a slide of cheese and respectively fastened to the top cover shell and the bottom cover shell on the inside and forced by the spring force of the spring plate to hold a cake of solid perfume in therebetween the bottom cover shell having a tongue with a hanging hole for hanging, and a retaining hole for fastening a clip.

BRIEF DESCRIPTION OF THE DRAWINGS

FIG. 1C is a side plain view of the top cover shell shown in FIG. 1A.

FIG. 2A is a top plain view of a bottom cover shell for an air freshener according to the present invention.

FIG. 2B is a bottom plain view of the bottom cover shell shown in FIG. 2A.

FIG. 3A illustrates the structure of a first clamping plate for an air freshener according to the present invention.

FIG. 3B is a bottom plain view of the first clamping plate shown in FIG. 3A.

FIG. 3C is a side plain view of the first clamping plate shown in FIG. 3A.

FIG. 3D is a top plain view of a second clamping plate for an air freshener according to the present invention.

FIG. 5A is a sectional assembly view of an air freshener according to the present invention.

FIG. 5B is a side plain view of the air freshener shown in FIG. 5A.

DETAILED DESCRIPTION OF THE PREFERRED EMBODIMENT

Figure 1A:
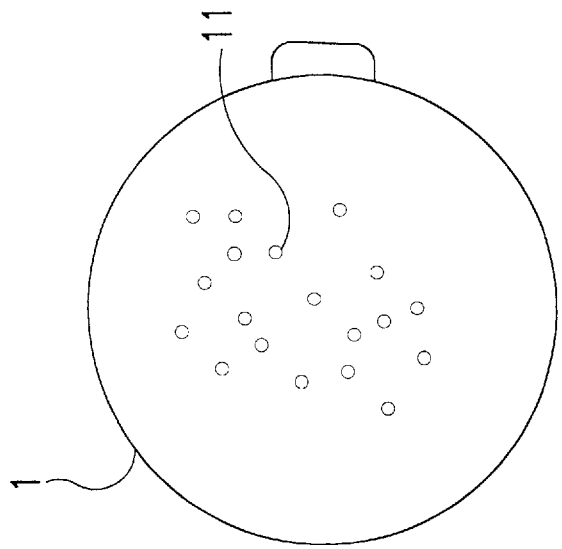
FIG. 1A is a top plain view of a top cover shell for an air freshener according to the present invention.
Figure 1B:
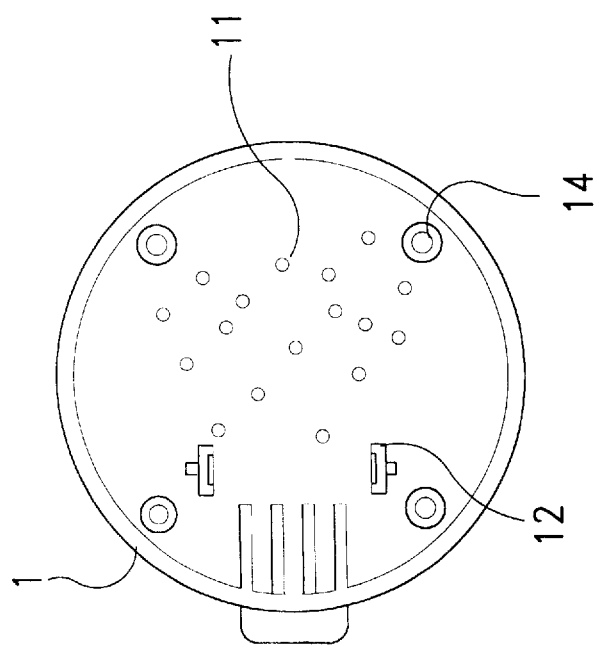
FIG. 1B is a bottom plain view of the top cover shell shown in FIG. 1A.
Figure 2C:
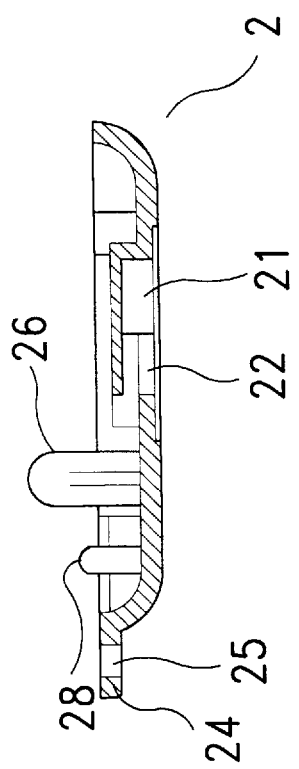
FIG. 2C is a side plain view of the bottom cover shell shown in FIG. 2A.

Referring to FIGS. from 1A to 1C, the top cover shell 1, referenced by 1, is shaped like a slice of bread, comprising a plurality of air vents 11, a plurality of downwardly extended coupling tube 14 raised from a bottom side wall thereof in four corners two downward lugs 12 raised from the bottom side wall and spaced between two coupling tube 14. The lugs 12 each have a pivot hole 13.

Referring to FIGS. from 2A to 2C, the bottom cover shell, referenced by 2, is shaped like a slice of bread, comprising an inside flange 22 defining a retaining hole 21, four upright coupling tubes 28 raised from a top side wall thereof in four corners, two upward lugs 26 vertically raised from the top side wall and spaced between two upright coupling tubes 28, the upward lugs 26 each having a hooked portion 27 sloping downwards from the top at an inner side, two through holes 23 respectively provided at the bottom ends of the upright coupling tube 28, a tongue 24 horizontally extended outwards from the periphery of the top side, a handing hole 25 at the tongue 24, and a necked locating rod 29 spaced between the through hole 25 and the inside flange 22.

Referring to FIGS. from 3A to 3C, the first clamping plate, referenced by 3, is shaped like a slice of cheese, comprising a notch 34 at one side, a plurality of protruded lines 33 raised from a top side wall thereof adjacent to one border side remote from the notch 24, a plurality of through holes 31 spaced between the notch 34 and the protruded lines 33, and a plurality of plug rods 32 raised from a bottom side wall thereof in four corners 32.

Referring to FIG. 3D, the second clamping plate, referenced by 7, is shaped like a piece of vegetable leaf, comprising a plurality of protruded lines 73 raised from a bottom side wall thereof adjacent to one border side, an opening 74, and a plurality of plug rods 72 downwardly extended from the bottom side wall in four corners.

Figure 4C:
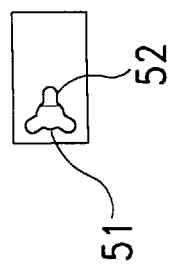
FIG. 4C is a bottom plain view in an enlarged scale of the spring plate shown in FIG. 4B.
Figure 4A:
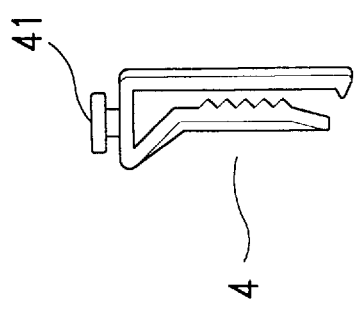
FIG. 4A illustrates the structure of a clip according to the present invention.

Referring to FIG. 4A, the clip 4 has a retainer rod 41 at one end.

Figure 4B:
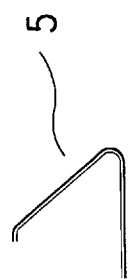
FIG. 4B is a side view of a spring plate for an air freshener according to the present invention.

Referring to FIGS. 4B and 4c, the spring plate, referenced by 5 has a substantially <-shaped profile, and a mounting hole 51 at one end. The mounting holes 51 has three angles 52.

The assembly process of the present invention is outlined hereinafter with reference to FIGS. 5A and 5B. The plug rods 72;32 of the clamping plates 7;3 are respectively plugged into the coupling tubes 14;28 of the cover shells 1;2, enabling the opening 74 of the second clamping plate 7 and the notch 34 of the first clamping plate 3 to be retained facing the tongue 24 of the bottom cover shell 2, then the mounting hole 51 of the spring plate 5 is coupled to the necked locating rod 29, enabling the neck of necked locating rod 29 to be forced into engagement with one angle 52 of the mounting hole 51 of the spring plate 5 to stop the spring plate 5 from a rotary motion, then the lugs 12 of the first cover shell 1 are respectively coupled to the lugs 26 of the second cover shell 2 by forcing the pivot holes 13 on the lugs 12 into engagement with the hooked portions 27 at the lugs 26, permitting the top end of the spring plate 5 to be stopped at the bottom side wall of the first cover shell 1. During the assembly process, a cake of solid perfume 6 is clamped between the clamping plates 7;3. When assembled. the air freshener is shaped like a hamburger. The retainer rod 41 of the aforesaid clip 4 can be fastened to the retaining hole 21 on the second cover shell 2 for securing the air freshener to for example the louvers of an air conditioner. When the air freshener is fastened to the louvers of an air conditioner by the clip 4, currents of air pass through the through holes 23 on the second cover shell 2, the through holes 31 on the first clamping plate 3, and the air vents 11 on the first cover shell 1. If the cake of solid perfume 6 is removed from the air freshener, the air freshener can be used as a paper clip. Furthermore, by means of the hanging hole 25 on the tongue 24 of the second cover shell 2, the air freshener can he hung for example on the inside of a car.

While only one embodiment of the present invention has been shown and described, it will be understood that various modifications and changes could be made thereunto without departing from the spirit and scope of the invention disclosed.

What the invention claimed is:

1. An air freshener comprising:

a top cover shell, said top cover shell comprising a plurality of air vents, a plurality of downwardly extended coupling tubes in four corners of a bottom side thereof, two downward lugs at one side defining a respective pivot hole;

a bottom cover shell pivoted to said top cover shell, said bottom cover shell comprising four upright coupling tubes raised from a top side wall thereof in four corners, two upward lugs vertically raised from the top side wall and spaced between two upright coupling tubes, said upward lugs each having a hooked portion sloping downwards and respectively hooked in the pivot holes on the downward lugs of said top cover shell, two through holes respectively provided at bottom ends of said upright coupling tubes, and a necked locating rod near the border thereof;

a first clamping plate, said first clamping plate comprising a notch at one side, a plurality of protruded lines raised from a top side wall thereof near an opposite side, a plurality of through holes spaced between the notch and the protruded lines of said first clamping plate, and a plurality of plug rods raised from a bottom side wall thereof in four corner and respectively plugged into the coupling tubes of said bottom cover shell;

a second clamping plate, said second clamping plate comprising a plurality of protruded lines raised from a bottom side wall thereof at one side, an opening, and a plurality of plug rods downwardly extended from the bottom side wall in four corners and respectively plugged into the coupling tubes of said top cover shell;

a spring plate having a first end, a mounting hole at said first end coupled to the necked locating rod of said bottom cover shell, and a second end inserted through the opening on said second clamping plate and stopped at the bottom side wall of said top cover shell, said spring plate imparting an upward pressure to one end of said top cover shell, causing said top cover shell to force said second clamping plate against said first clamping plate for permitting a cake of solid perfume to be clamped in between said first clamping plate and said second clamping plate.

2. The air freshener of claim 1 wherein said bottom cover shell comprises an inside flange defining a retaining hole for mounting a clip for fastening.

3. The air freshener of claim 1 wherein said bottom cover shell comprises an outwardly extended tongue, and a handing hole one said outwardly extended tongue for hanging.

* * * * *